(12) United States Patent
Park et al.

(10) Patent No.: US 10,988,731 B2
(45) Date of Patent: Apr. 27, 2021

(54) FORMULATION FOR STORAGE, TRANSPORTATION, AND DELIVERY OF PROTEIN RICH CONDITIONED MEDIUM

(71) Applicant: HOPE BIOSCIENCES, LLC, Sugar Land, TX (US)

(72) Inventors: Hyeonggeun Park, Sugar Land, TX (US); Fred Haisam Khoury, Porter Ranch, CA (US)

(73) Assignee: HOPE BIOSCIENCES, LLC, Sugar Land, TX (US)

( * ) Notice: Subject to any disclaimer, the term of this patent is extended or adjusted under 35 U.S.C. 154(b) by 0 days.

(21) Appl. No.: 15/836,487

(22) Filed: Dec. 8, 2017

(65) Prior Publication Data

US 2018/0100138 A1 Apr. 12, 2018

Related U.S. Application Data

(63) Continuation-in-part of application No. 15/460,111, filed on Mar. 15, 2017, which is a continuation-in-part of application No. 15/142,135, filed on Apr. 29, 2016.

(51) Int. Cl.
| | |
|---|---|
| *C12N 5/00* | (2006.01) |
| *C12N 5/0775* | (2010.01) |
| *A61K 35/28* | (2015.01) |

(52) U.S. Cl.
CPC ......... *C12N 5/0018* (2013.01); *C12N 5/0068* (2013.01); *C12N 5/0662* (2013.01); *C12N 5/0667* (2013.01); *A61K 35/28* (2013.01); *C12N 2500/99* (2013.01)

(58) Field of Classification Search
CPC .. C12N 5/0018; C12N 5/0068; C12N 5/0662; C12N 5/0067; C12N 2500/99; A61K 35/28
USPC ........................................................ 435/326
See application file for complete search history.

(56) References Cited

U.S. PATENT DOCUMENTS

| | | | |
|---|---|---|---|
| 7,807,461 B2 | 10/2010 | Kang et al. | |
| 8,252,591 B2 | 8/2012 | Ince et al. | |
| 9,034,833 B1* | 5/2015 | Chiou | A61K 8/891 514/25 |
| 2004/0037811 A1 | 2/2004 | Penn et al. | |
| 2007/0128685 A1 | 6/2007 | Faudoa et al. | |
| 2008/0085555 A1 | 4/2008 | Asahara et al. | |
| 2012/0301411 A1* | 11/2012 | Ludwig | A61K 8/34 424/59 |
| 2013/0058903 A1* | 3/2013 | Lee | C12N 5/0663 424/93.7 |
| 2013/0089928 A1 | 4/2013 | An et al. | |
| 2014/0140950 A1* | 5/2014 | Arnone | A61K 8/64 424/85.2 |
| 2014/0309173 A1* | 10/2014 | Dreher | A61K 8/64 514/18.8 |
| 2016/0206550 A1* | 7/2016 | Balasubramanian | C12N 5/0663 |

FOREIGN PATENT DOCUMENTS

| | | |
|---|---|---|
| WO | 2007123363 A1 | 11/2007 |
| WO | 2013032052 A1 | 3/2013 |

OTHER PUBLICATIONS

Wager, et al. Replicative Senescence of Mesenchymal Stem Cells: A Continuous and Organized Process, PLoS ONE. 3(5):e2213 (2008).

* cited by examiner

*Primary Examiner* — Jennifer M. H. Tichy
(74) *Attorney, Agent, or Firm* — Rao DeBoer Osterrieder, PLLC; Dileep P. Rao

(57) ABSTRACT

A method of creating a protein rich conditioned medium. The method includes culturing mesenchymal stem cells in a container utilizing a first growth medium, allowing a time period for proliferation of the mesenchymal stem cells until a desired level of confluence is achieved in the container, discarding a supernatant from the container, adding a second medium to the container, incubating the mesenchymal stem cells, and collecting the conditioned medium. The method produces significantly higher quantities of byproducts secreted by the mesenchymal stem cells. Byproducts are usable for wound healing, disease treatment, cosmetic, or other beneficial effects when applied or otherwise delivered to a patient.

8 Claims, 1 Drawing Sheet

| INGREDIENT | SAMPLE EMBODIMENT (%W/W) | ACCEPTABLE RANGES (%W/W) |
|---|---|---|
| CONDITIONED MEDIUM | 50.000 | 0.01 - 99.00 |
| DILUENT | 39.100 | 0.01 - 80.00 |
| CHELATOR | 0.100 | 0.01 - 0.30 |
| HUMECTANT / SOLVENT | 3.000 | 0.01 - 30.00 |
| PRESERVATIVE / PRESERVATIVE BOOSTER | 1.000 | 0.01 - 1.05 |
| EMOLLIENT | 5.000 | 0.1 - 30.00 |
| THICKENER / EMULSIFIER / STABILIZER | 1.800 | 0.01 - 5.00 |

FORMULATION FOR STORAGE, TRANSPORTATION, AND DELIVERY OF PROTEIN RICH CONDITIONED MEDIUM

CROSS REFERENCE TO RELATED APPLICATIONS

The current application is a Continuation in Part and claims priority to co-pending U.S. patent application Ser. No. 15/460,111 filed on Mar. 15, 2017, titled "METHOD FOR GENERATING PROTEIN RICH CONDITIONED MEDIUM", which in turn is a Continuation in Part and claims priority to co-pending U.S. patent application Ser. No. 15/142,135 filed on Apr. 29, 2016, titled "CULTURE MEDIA FOR MULTIPOTENT STEM CELLS". These references are hereby incorporated in their entirety.

FIELD

The present disclosure addresses a formulation comprising conditioned media which protects the conditioned media and allows for effective topical delivery of the conditioned media.

BACKGROUND

Mesenchymal stem cells (MSCs) are a specific group of mesoderm origin adult stem cells that are pluripotent. Being pluripotent, they have multi-directional differentiation capabilities. They can become fat, bone, cartilage, tendons, muscle, nerves, ligaments, liver, cardiac muscle, endothelial cells, pancreatic islet cells and many others. In addition, they are cells with low immunogenicity and are naturally immune-modulatory cells. Given their versatility, MSCs have quickly become an ideal cell type used in therapeutics for degenerative and autoimmune conditions, amongst other ailments.

When culturing MSCs in a growth medium, protein byproducts and non-protein byproducts are secreted by the MSCs as they proliferate and continue to be secreted when MSCs have been cultured. The protein byproducts can have significant wound healing, disease treatment, cosmetic, or other beneficial effects when applied or otherwise delivered to a patient. A medium containing such byproducts can be referred to as a conditioned medium.

The protein byproducts have the benefit of being the pure active ingredient desirable for medical treatments or cosmetic applications. Further, the protein byproducts are sterile and safe to use in virtually any circumstance.

While usage of a conditioned medium and creation thereof is known in the art, storage of the conditioned medium and delivery to a patient is problematic due to a liquid consistency of the conditioned medium, short shelf life, temperature instability, and denaturing of proteins within the conditioned medium over time.

A need exists for a stable storage means to stabilize and preserve the conditioned medium. A further need exists for an effective delivery mechanism to the patient.

The present disclosure fulfils the above needs with a formulation for the storage, transportation, and delivery of a conditioned medium.

BRIEF DESCRIPTION OF THE DRAWINGS

The detailed description will be better understood in conjunction with the accompanying drawing as follows:

The FIGURE is a chart illustrating one embodiment of the present invention and the ingredient ranges usable with the present disclosure.

The present embodiments are detailed below with reference to the listed FIGURE.

DETAILED DESCRIPTION OF THE EMBODIMENTS

Before explaining the present invention in detail, it is to be understood that the invention is not limited to the specifics of particular embodiments as described and that it can be practiced, constructed, or carried out in various ways.

While embodiments of the disclosure have been shown and described, modifications thereof can be made by one skilled in the art without departing from the spirit and teachings of the disclosure. The embodiments described herein are exemplary only, and are not intended to be limiting.

Specific structural and functional details disclosed herein are not to be interpreted as limiting, but merely as a basis of the claims and as a representative basis for teaching persons having ordinary skill in the art to variously employ the present invention. Many variations and modifications of embodiments disclosed herein are possible and are within the scope of the present disclosure.

Where numerical ranges or limitations are expressly stated, such express ranges or limitations should be understood to include iterative ranges or limitations of like magnitude falling within the expressly stated ranges or limitations.

The use of the word "a" or "an" when used in conjunction with the term "comprising" in the claims and/or the specification may mean "one," but it is also consistent with the meaning of "one or more," "at least one," and "one or more than one."

The word "about" means plus or minus 5 percent of the stated number.

The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description herein, but is only limited by the claims which follow, encompassing all equivalents of the subject matter of the claims. Each and every claim is incorporated into the specification as an embodiment of the present disclosure. Thus, the claims are a further description and are an addition to the preferred embodiments of the present disclosure.

The inclusion or discussion of a reference is not an admission that it is prior art to the present disclosure, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

The present embodiments generally relate to creating a storage, transportation, and delivery formulation comprising a protein rich conditioned medium from media used for culturing mesenchymal stem cells (MSCs). While human stem cells are the subject of the present disclosure, it is contemplated that all mammalian stem cells would respond to the culture as disclosed and the storage, transportation, and delivery medium would be equally applicable to all derived conditioned media. In the spirit of enablement and clarity, human stem cells are utilized to describe the invention below.

Conditioned medium has a wide range of health benefits, many of which can be realized when topically applied to skin. The protein rich ingredients have highly beneficial wound healing and cosmetic benefits. However, the liquid consistency and relative fragility of the conditioned medium makes it difficult to use because of difficulties transporting and storing it. Further, application to skin is problematic due to difficulty in keeping the conditioned medium at the desired point of contact.

The present disclosure addresses a formulation comprising conditioned media which protects the conditioned media and allows for effective topical delivery of the conditioned media.

Exemplary proteins secreted by MSCs include, but are not limited to: Keratinocyte growth factor (KGF)(for example growth factor FGF7), Insulin-like growth factors (IGFs), Vascular endothelial growth factor (VEGF)(originally known as vascular permeability factor (VPF)), Epidermal growth factor (EGF), Hepatocyte growth factor (HGF) (or scatter factor (SF)), Stromal cell derived factor (SDF), Transforming growth factor (TGF), Collagen and pre-collagen components such as procollagen, and Fibronectin.

Serum, as used within this disclosure, refers to the remaining fraction after removal of coagulation and red blood cells from any mammalian blood. Exemplary serums used for cell culture as known to persons having ordinary skill in the art include, but are not limited to: fetal bovine serum (also known as fetal calf serum), horse serum, mouse serum, goat serum, rabbit serum, rat serum, human serum, and the like. Serum is also intended to encompass synthetic or recombinant equivalents, or other equivalents as known to persons having ordinary skill in the art, such as Human Platelet Lysate (hPL).

Fibroblast growth factors and epidermal growth factors, as used within this disclosure, refers to families of proteins, hormones, or other naturally occurring substances that promote cell growth, proliferation, and/or differentiation. Members are typically involved in angiogenesis, wound healing, embryonic development, and various endocrine signaling pathways. Synthetic, recombinant, or other equivalents are also covered within the scope of this disclosure.

Pituitary extract, as used within this disclosure, refers to hormones extracted from the pituitary gland, such as oxytocin or vasopressin. Any mammalian pituitary extracts and their equivalents can be utilized. Synthetic, recombinant, or other equivalents are also covered within the scope of this disclosure.

L-Cysteine, as used within this disclosure, refers to the amino acid as known to persons having ordinary skill in the art. Synthetic, recombinant, or other equivalents are also covered within the scope of this disclosure.

Glutathione, as used within this disclosure, refers to an antioxidant found in plants, animals, fungi, bacteria, or other living organisms. Synthetic, recombinant, or other equivalents are also covered within the scope of this disclosure.

N-Acetyl Cysteine (NAC), as used within this disclosure, refers to a protein that potentially participates in self-renewal and pluripotency in stem cells. Synthetic, recombinant, or other equivalents are also covered within the scope of this disclosure.

Selenium, as used within this disclosure, refers to the non-metal chemical element with the symbol Se. Synthetic, recombinant, or other equivalents are also covered within the scope of this disclosure.

Stromal-derived factor, as used within this disclosure, refers to proteins belonging to the chemokine family which promote growth, survival, and development of stem cells. Synthetic, recombinant, or other equivalents are also covered within the scope of this disclosure.

Sodium pyruvate, as used within this disclosure, refers to a compound commonly added to cell culture media to provide an additional source of energy. Synthetic, recombinant, or other equivalents are also covered within the scope of this disclosure.

Transferrin, as used within this disclosure, refers to iron binding proteins commonly found in blood. Any mammalian transferrin and equivalents can be utilized. Synthetic, recombinant, or other equivalents are also covered within the scope of this disclosure.

Serum-free medium, as used within this disclosure, refers to a basal medium. A basal medium can be any medium designed to support the growth of microorganisms or cells.

An exemplary method of creating a protein rich conditioned medium can have the following steps:

Culturing mesenchymal stem cells in a container utilizing a first growth medium. Any container known to persons having ordinary skill in the art can be utilized. The first growth medium can comprise a serum, a fibroblast growth factor, and either an L-cysteine, a glutathione, or a N Acetyl Cysteine (NAC). While the disclosure emphasizes the use of adipose derived stem cells, any MSC can be utilized for culture.

Optionally, the first growth medium can also contain various quantities of an epidermal growth factor, a hydrocortisone, a calcium chloride, an insulin, a pituitary extract, a selenium, a stromal-derived factor, a sodium pyruvate, a transferrin, and serum-free medium.

Allowing a time period for proliferation of the mesenchymal stem cells until a desired level of confluence is achieved in the container. Confluence in this disclosure refers to the proportion or percentage of the container surface covered by MSCs.

Discarding a supernatant from the container, thereby removing the first growth medium.

Optionally, washing the MSCs in the container with a salt buffered solution.

Adding a second medium to the container. The second medium can be a serum-free medium, or a salt buffered solution. In embodiments, the salt used can be a calcium salt or a magnesium salt.

The second medium typically does not contain components encouraging the MSCs to proliferate. This allows for all of the MSC resources to be devoted to secreting protein or non-protein byproducts instead of reproducing, thereby maximizing the quantity of byproducts.

Incubating the mesenchymal stem cells and the second medium for a desired period of time, thereby creating a conditioned medium. Persons having ordinary skill in the art can adjust incubation times and temperatures for optimal results. A typical set of parameters can be at a temperature from about 35 degrees Celsius to about 40 degrees Celsius for a period of about 1 day to about 7 days.

While typically, the vast majority of the results are achieved within 2 days of incubation, longer periods can be implemented as necessary without detriment to either the MSCs or the protein byproducts. Time frames of up to 30 days have been tested, at which point MSCs start to die within the culture.

Further, as known in the art, stressing the MSCs, such as by removing the food source can accelerate protein byproduct production. During incubation, subjecting the MSCs to environmental or mechanical stresses may further enhance byproduct secretion by the MSCs. Exemplary stresses include, but are not limited to: starving the MSCs, manipulating the temperature, manipulating the atmosphere, vibrating the container, spinning the container, or other methods known to persons having ordinary skill in the art.

Collecting the conditioned medium by decanting the supernatant.

Optionally, the conditioned medium can be subjected to a process to remove cellular debris, such as centrifuging the conditioned medium for a duration at a desired speed. Persons having ordinary skill in the art can select from any known methods and parameters for removing cellular debris.

Optionally, filtering the conditioned medium to remove debris. In embodiments, the filter can have a pore size ranging from 0.1 μm to 0.45 μm.

The conditioned medium contains various protein byproducts produced by the MSCs. Exemplary proteins include, but are not limited to: Keratinocyte growth factor (KGF)(for example growth factor FGF7), Insulin-like growth factors (IGFs), Vascular endothelial growth factor (VEGF)(originally known as vascular permeability factor (VPF)), Epidermal growth factor (EGF), Hepatocyte growth factor (HGF) (or scatter factor (SF)), Stromal cell derived factor (SDF), Transforming growth factor (TGF), Collagen and pre-collagen components, and Fibronectin.

While protein byproducts are discussed within the present disclosure, other beneficial non-protein byproducts may be secreted by the MSCs.

The present invention leads to much greater yields of the protein byproducts than by utilizing methods currently known in the art. The growth medium as disclosed allows for MSCs to proliferate without degrading, thereby continuing to produce protein byproducts recovered in the conditioned medium.

EXAMPLE EMBODIMENT

Human adipose tissue-derived mesenchymal stem cells were cultured with a first growth medium containing fetal bovine serum, a fibroblast growth factor, and either L-Cysteine, Glutathione, or NAC in a normal cell culture environment. Temperature was maintained at 37 degrees Celsius, with a carbon dioxide concentration of 5 percent.

Upon reaching a confluence of at least 90 percent, the supernatant was discarded and the cultured MSCs were washed with a salt buffered solution. The salt buffered solution contained Calcium and Magnesium salts.

After washing the MSCs, a second medium (serum free medium) was added to the cultured MSCs.

The MSCs were incubated for approximately 2 days in normal cell culture environment to allow for the secretion of protein byproducts into the second medium. The second medium was then collected as the conditioned medium.

In this instance, the conditioned medium was centrifuged for 10 minutes at 2000 revolutions per minute in order to remove cellular debris.

In this instance, the conditioned medium was further filtered for purification, thereby creating the final conditioned medium.

The final conditioned medium was then processed for storage, transportation, and delivery by creating a formulation with various ingredients, as discussed below.

A storage, transportation, and delivery formulation can be created utilizing the following ingredients in combination with the conditioned medium: a diluent, a chelator, a humectant or a solvent, a preservative, an emollient, and an emulsifier. In embodiments, a preservative booster can also be added.

The formulation can include a diluent to achieve a desired consistency. A typical diluent used in cosmetics or products applied to the skin is water in various forms, such as tap water, distilled water, deionized water, demineralized water, deionized and demineralized water, mineral water, botanical water, or combinations thereof. Additional equivalent diluents as applicable for specific applications can be substituted as determined by persons having ordinary skill in the art.

The formulation can include a chelator or a chelating agent to bond with metal ions. A typical function is to prevent contamination of the formulation, as well as to prevent discoloration over time. Ethylenediaminetetraacetic acid (EDTA) is a commonly used chelator for cations. Various forms of EDTA, such as disodium EDTA or calcium disodium EDTA can be used in the formulation. Based upon specific requirements, other usable chelators include, but are not limited to: phytic acid, phytic acid salts, tetrasodium glutamate diacetate, etidronic acid, trisodium ethylenediamine disuccinate, or combinations thereof. Additional equivalent chelators as applicable for specific applications can be substituted as determined by persons having ordinary skill in the art.

The formulation can include a humectant or a solvent to keep the formulation moist. In specific applications, the humectant can also serve to increase the solubility of various components of the formulation to aid in penetrating the skin or increasing activity time for ingredients. Usable humectants or solvents include, but are not limited to: propanediol, an alcohol, a glycol, a glycerol, sorbitol, or combinations thereof.

The formulation can include a preservative and, optionally, a preservative booster to prolong the useful life of ingredients within the formulation. Usable preservatives and preservative boosters include, but are not limited to: phenoxyethanol, ethylhexylglycerin, phenethyl alcohol, a glycol, an alcohol, or combinations thereof.

The formulation can include an emollient to help soften and smooth skin. Usable emollients include, but are not limited to: C12-15 alkyl benzoate, isopropyl palmitate, sunflower seed oil, dimethicone, isohexadecane, polyisobutane, mineral oil, squalene, squalene, or combinations thereof.

The formulation can include an emulsifier to thicken and kinetically stabilize the formulation. A commonly used emulsifier is a surfactant. Usable emulsifiers include, but are not limited to: polyacrylate crosspolymer-6, a cellulose, a carbomer, a polyacrylate, acrylates/C10-30 alkyl acrylate crosspolymer, xanthan gum, a carrageenan, a polyurethane, PVP acrylates copolymer, polyquaternium-10, or combinations thereof.

While specific functionalities have been discussed of the various ingredients above, it should be noted that the ingredients can serve multiple purposes within the formulation. Further, creation of microemulsions and nanoemulsions, adjustment of pH ranges, addition of fragrances, addition of colorings, addition of anti-oxidants, addition of anti-allergens, and the like are all included within the spirit of the embodied disclosure. Various additional ingredients may be added for cosmetic and/or health reasons by persons having ordinary skill in the art.

It should also be noted that, while typical ingredients are disclosed for enabling purposes above, persons having ordinary skill in the art will be aware of a wide range of equivalents and substitutable components that can be used without exceeding the scope of this disclosure.

The FIGURE is a chart illustrating one embodiment of the present invention and the ingredient ranges usable with the present disclosure. It should be noted that the overall concentration of the preservative and preservative booster (if used) will remain within the range of 0.01-1.05 percent weight by weight.

While the disclosure has emphasized the presented embodiments and FIGURE, it should be understood that within the scope of the appended claims, the disclosure might be embodied other than as specifically enabled herein.

What is claimed is:

1. A storage, transportation, and delivery formulation comprising a protein rich conditioned medium comprising:
    a) a conditioned medium comprising at least:
        i) 0.3 pg/ml fibroblast growth factor (FGF);
        ii) 6 pg/ml transforming growth factor (TGF);
        iii) 6 pg/ml epidermal growth factor (EGF), wherein the epidermal growth factor (EGF) is present in at least twenty times the concentration of fibroblast growth factor (FGF); and
        iv) 300 pg/ml stromal-derived factor (SDF);
    b) water;
    c) disodium ethylenediaminetetraacetic acid;
    d) propanediol;
    e) phenoxyethanol;
    f) C12-15 alkyl benzoate; and
    g) polyacrylate Crosspolymer-6; and
    wherein the conditioned medium is not concentrated.

2. The formulation of claim 1, further comprising ethylhexylglycerin.

3. The formulation of claim 1, wherein the conditioned medium further comprises at least:
    a) 1 ng/ml keratinocyte growth factor (KGF);
    b) 1.5 ng/ml insulin-like growth factor (IGF);
    c) 6 ng/ml vascular endothelial growth factor (VEGF); and
    d) 9 ng/ml hepatocyte growth factor (HGF).

4. The formulation of claim 1, wherein the percent weight by weight of each component is:
    a) conditioned medium from 0.01% to 99.00%;
    b) water from 0.01% to 80.00%;
    c) disodium ethylenediaminetetraacetic acid from 0.01% to 30%;
    d) propanediol from 0.01% to 30.00%;
    e) phenoxyethanol from 0.01% to 1.05%;
    f) C12-15 alkyl benzoate from 0.10% to 30.00%; and
    g) polyacrylate crosspolymer-6 from 0.01% to 5.00%.

5. The formulation of claim 1, further comprising a preservative booster.

6. The formulation of claim 5, wherein the preservative booster is:
    a) ethylhexylglycerin;
    b) phenethyl alcohol;
    c) a glycol;
    d) an alcohol; or
    e) combinations thereof.

7. The formulation of claim 6, wherein the percent weight by weight of the phenoxyethanol and the preservative booster combined is from 0.01% to 1.05% weight by weight.

8. A method of creating a storage, transportation, and delivery formulation comprising a protein rich conditioned medium, the method comprising:
    a) culturing mesenchymal stem cells;
    b) collecting a conditioned medium comprising at least:
        i) 0.3 pg/ml fibroblast growth factor (FGF);
        ii) 6 pg/ml transforming growth factor (TGF);
        iii) 6 pg/ml epidermal growth factor (EGF), wherein the epidermal growth factor (EGF) is present in at least twenty times the concentration of fibroblast growth factor (FGF); and
        iv) 300 pg/ml stromal-derived factor (SDF); and
    c) combining the conditioned medium with:
        i) water from 0.01% to 80.00%;
        ii) disodium ethylenediaminetetraacetic acid from 0.01% to 30%;
        iii) propanediol from 0.01% to 30.00%;
        iv) phenoxyethanol from 0.01% to 1.05%;
        v) C12-15 alkyl benzoate from 0.10% to 30.00%; and
        vi) polyacrylate crosspolymer-6 from 0.01% to 5.00%;
    wherein the conditioned medium is not concentrated; and
    wherein the formulation forms an emulsion for storage, transportation, and delivery of the conditioned medium.

* * * * *